(12) United States Patent
Cockrem (10) Patent No.: US 6,291,708 B1
(45) Date of Patent: Sep. 18, 2001

(54) PROCESS FOR PRODUCTION OF ORGANIC ACIDS AND ESTERS THEREOF

(75) Inventor: Michael Charles Milner Cockrem, Madison, WI (US)

(73) Assignee: A.E. Staley Manufacturing Co., Decatur, IL (US)

( * ) Notice: Subject to any disclaimer, the term of this patent is extended or adjusted under 35 U.S.C. 154(b) by 0 days.

(21) Appl. No.: 09/301,466

(22) Filed: Apr. 28, 1999

(51) Int. Cl.$^7$ .................................................. C07C 59/08
(52) U.S. Cl. ........................... 562/589; 562/580; 560/179
(58) Field of Search ................... 562/580, 589; 560/179

(56) References Cited

U.S. PATENT DOCUMENTS

| | | |
|---|---|---|
| 1,668,806 | 5/1928 | Gabriel et al. . |
| 2,029,694 | 2/1936 | Bannister ............................. 260/106 |
| 2,334,524 | 11/1943 | Wenker ................................ 260/535 |
| 2,465,772 | 3/1949 | Weisberg et al. .................... 260/484 |
| 2,565,487 | 8/1951 | Filachione et al. .................. 260/484 |

(List continued on next page.)

FOREIGN PATENT DOCUMENTS

0614983 A * 9/1994 (EP) .

OTHER PUBLICATIONS

Filachione et al., "Lactic Esters by Reaction of Ammonium Lactate with Alcohols," *Industrial and Engineering Chemistry*, pp 2189–2191 (Sep. 1952).
Costello et al., "Preparation and Properties of Pure Ammonium DL–Lactate," *Journal of the American Chemical Society* 75:1242–1244 (Mar. 1953).
Opsahl, "Fatty Acid Amides,", *Encyclopedia of Chemical Technology* 2:346–356 (1992).
Coleman et al., "Acetamide," *Organic Syntheses* 1:3–4.
House, Jr., "Decomposition of Ammonium Carbonate and Ammonium Bicarbonate and Proton Affinities of the Anions," *Inorg. Nucl. Chem. Letters* 16:185–187 (1980).
House, Jr. et al., "TG Studies on the Decomposition of Some Ammonium Compounds," *Thermochimica Acta* 42:377–381 (1980).
Filachione et al., "Purification of Lactic Acid," *Industrial and Engineering Chemistry* 38:228–232 (1946).
Derwent Abstract DD 206373 (1984).

*Primary Examiner*—Paul J. Killos
*Assistant Examiner*—Taylor V Oh
(74) *Attorney, Agent, or Firm*—Williams, Morgan & Amerson, P.C.

(57) ABSTRACT

A process is disclosed for producing an organic acid and optionally for simultaneously producing an ester of the organic acid. The process comprises the steps of: (a) combining an aqueous diluent, an ammonium salt of an organic acid, and an alcohol, thereby forming a homogeneous liquid feed mixture; (b) rapidly heating the feed mixture at a pressure sufficient to suppress at least some vaporization of the alcohol and holding it at a temperature and for a time sufficient to decompose the ammonium salt of the organic acid into ammonia and free organic acid while rapidly removing the ammonia from the reaction-mass transfer equipment, and optionally to react at least some of the free organic acid with the alcohol to form an ester of the organic acid, thereby producing (i) a vapor product stream that comprises ammonia, water, and alcohol, and (ii) a liquid product stream that comprises free organic acid, optionally ester, and alcohol, where of the total quantity of alcohol in the vapor product stream and the liquid product stream, at least about 10% by weight is present in the liquid product stream; and (c) recovering the free organic acid and optionally the ester from the liquid product stream. The liquid feed mixture can comprise a concentrated crude or partially purified broth produced by a fermentation process.

43 Claims, 1 Drawing Sheet

U.S. PATENT DOCUMENTS

| | | | |
|---|---|---|---|
| 2,722,541 | 11/1955 | Schulz, Jr. et al. | 260/484 |
| 4,100,189 | 7/1978 | Merciir | 260/541 |
| 4,444,881 * | 4/1984 | Urbas | 435/139 |
| 5,071,754 | 12/1991 | Walkup et al. | 435/135 |
| 5,210,296 * | 5/1993 | Cockrem et al. | 562/589 |
| 5,252,473 * | 10/1993 | Walkup et al. | 435/135 |
| 5,426,219 | 6/1995 | Lehnhardt et al. | 562/580 |
| 5,453,365 * | 9/1995 | Sterzel et al. | 435/135 |
| 5,510,526 * | 4/1996 | Baniel et al. | 562/580 |
| 5,723,639 | 3/1998 | Datta et al. | 554/154 |
| 5,766,439 * | 6/1998 | Eyal et al. | 204/524 |

* cited by examiner

Figure 1

PROCESS FOR PRODUCTION OF ORGANIC ACIDS AND ESTERS THEREOF

BACKGROUND OF THE INVENTION

The present invention relates to processes for producing and recovering an organic acid, such as lactic acid, and esters thereof.

Organic acids such as lactic acid have a number of commercial uses, for example in food manufacturing, pharmaceuticals, plastics, textiles, and as a starting material in various chemical processes. It is well known to produce organic acids by fermentation of sugars, starch, or cheese whey, using microorganisms such as *Lactobacillus delbrueckii* to convert monosaccharides such as glucose, fructose, or galactose, or disaccharides such as sucrose or lactose, into organic acids such as lactic acid. The broth that results from fermentation contains unfermented sugars, carbohydrates, amino acids, proteins, and salts, as well as the acid. Some of these materials cause an undesirable color. The acid usually therefore must be recovered from the fermentation broth before it can be put to any substantial use.

During the production of an organic acid such as lactic acid by fermentation, the increasing concentration of the acid in the fermentation broth reduces the pH. As the pH decreases, the growth of the microorganism is inhibited and eventually stops, and therefore acid production stops. To prevent this, the pH of the fermentation broth typically is controlled by adding a base for neutralization, such as ammonia or a sodium or calcium base. However, one result of the addition of such a base is the formation of a salt of the acid (e.g., ammonium lactate). Therefore, it is often necessary to convert the salt to free acid or another form such as an ester, which subsequently can be converted to the free acid. The formation of the free acid we term here "acidification". The production of the ester can be advantageous as the ester can be distilled to produce a product of very high purity, which can then subsequently be converted back to a free acid of high purity. This serves to meet another of the process objectives, which we term "purification".

Many different processes have been suggested to convert the salt to free acid, including addition of a strong acid such as sulfuric acid followed by precipitation of the formed salt such as calcium sulfate; ion exchange; electrodialysis; and other methods. Many of these methods have the disadvantage of producing large quantities of waste or by-product such as calcium sulfate.

Other methods for conversion of the salt of the acid into free acid tend to be expensive. Electrodialysis for conversion of salts of organic acids into free organic acid and free base solution is expensive in both capital and operating costs. Another method that has been proposed involves the use of high pressure carbon dioxide in the presence of an amine extractant. This is cheaper than electrodialysis but is rather complex and may be difficult to operate.

Lactic acid is one organic acid of particular interest today because of a great projected demand for use as a polymer feedstock. As mentioned above, production of lactic acid by fermentation is most efficient at a pH range where the lactic acid is largely present as a salt. Thus recovery of pure lactic acid requires conversion of the salt into free acid. Purification steps are also required. One such method is production of a lactate ester and purification of the ester. Esters are organic chemicals of significant industrial importance, for example for use as solvents and as reagents. One way to form esters is by reacting an organic acid with an alcohol to form an ester and water, as shown in reaction (1):

$$R_1\text{—COOH} + R_2\text{—CH}_2\text{OH} \leftrightharpoons R_1\text{—COO—CH}_2R_2 + H_2O$$

organic acid+alcohol⇌ester+water     Reaction (1)

Many esterification processes or systems focus on removal of water to drive the yield or conversion. Removal of water biases the equilibrium towards the products shown on the right hand side of Equation (1). This approach to esterification has been successfully applied to a wide range of organic acids and alcohols.

Ammonium salts of organic acids can be esterified as follows:

$$R_1\text{—COO}^-\text{NH}_4^{++}R_2\text{—CH}_2H \leftrightharpoons R_1\text{—COO—CH}_2R_2 + NH_3 + H_2O$$

ammonium salt of organic acid+alcohol⇌ester+ammonia+water     Reaction (2)

In this process, the ammonia and the water are ideally removed from the reaction medium to enhance the rate of reaction.

However, a reaction that is known to proceed quite readily is the following:

$$R_1\text{-COOH} + NH_3 \leftrightharpoons R_1\text{—CONH}_2 + H_2O$$

organic acid+ammonia⇌amide+water     Reaction (3)

Another reaction that can occur is:

ester+ammonia⇌amide+alcohol     Reaction (4)

This is usually considered an unwanted side reaction.

Another reaction that can take place involves alcoholysis of an amide, which can be acid catalyzed:

amide+alcohol⇌ester+ammonia     Reaction (5)

This reaction tends to proceed rather slowly and is not expected to be part of reaction (2). However, it can be a useful side reaction.

Another reaction that may occur is:

ammonia+acid⇌ammonium salt     Reaction (6)

This reaction may occur as part of reaction (2).

The amide is usually an undesirable product in organic acid manufacturing. Prior attempts to make reaction (2) proceed successfully have been restricted in yield by the tendency for reaction (3) to occur at the same time. Additionally, in normal operation in systems at ambient temperature reaction (2) proceeds relatively slowly.

A number of researchers have attempted to develop methods for conversion of ammonium salts into free acids or esters.

Filachione and Costello (Industrial Engineering and Chemistry Volume 44, Page 2189, 1952) describe a method for esterification of ammonium lactate directly with butanol or other alcohols with four or more carbon atoms. For example, an aqueous ammonium lactate solution and n-butanol were charged to a reactor vessel and refluxed for 4 to 8 hours at 105 to 145° C. Typically during the course of the batch run the temperature rose, as water was slowly removed, driving the reaction towards the n-butyl lactate product. Ammonia and water products were taken off overhead together with the n-butanol—water azeotrope. The heterogeneous azeotroping agent was condensed, the alcohol phase returned to the reactor, and the water phase with dissolved ammonia was removed. The process achieved from 61 to 92% ammonia removal and from 49 to 67% conversion to butyl lactate. When the process used residue from previous steps, only part of the residue was recovered. An unwanted, yield reducing by-product builds up in the system. Filachione et al (U.S. Pat. No. 2,565,487, Aug. 28, 1951) also describe this direct esterification process.

It should be noted that lower alcohols can be used for esterification if benzene or some other azeotroping agent is added to the mixture. In these cases, the benzene-water forms the overhead heterogeneous azeotrope that is used to remove water to drive the reaction.

This process is not economical or practical due to the buildup of unwanted side reaction products, the long reaction times, and the relatively poor yields. For the case with ethanol, the added heterogeneous azeotroping agent adds to process complexity and safety concerns.

Schulz et al (U.S. Pat. No. 2,722,541, Nov. 1, 1955) describe equipment and a process to react ammonium lactate with butanol to make butyl lactate. They use several countercurrent reactors in series rather than the single reactor used by Filachione et al. However, they do not achieve significantly better yields or rates than Filachione et al.

Mercier (U.S. Pat. No. 4,100,189, Jul. 11, 1978) describes a process for recovery of free acetic acid. This process commences with the extraction of free acetic acid into a solvent, butyl-acetate mixed with n-butanol, which also will later act as an azeotroping agent for water removal. After the initial solvent extraction, Mercier back extracts the free acetic acid into ammonia and generates an aqueous ammonium acetate solution. This solution is then thermally decomposed to give ammonia and acetic acid in part of a complex system of columns and recycles. The decomposition temperature is 90 to 130° C. The formation of esters and the formation of side reaction products is not addressed in this patent.

Walkup et al (U.S. Pat. No. 5,071,754, Dec. 10, 1991, and U.S. Pat. No. 5,252,473, Oct. 12, 1993) propose a process wherein ammonium lactate is reacted with alcohol in presence of stoichiometric excess gaseous carbon dioxide. An overhead gas stream containing carbon dioxide and ammonia is drawn off. A heavy bottoms stream is produced that contains the lactate ester. This is very similar to the direct esterification of ammonium lactate, as reported by Filachione et al. The added carbon dioxide acts to reduce the reaction time by providing an acidic material to help produce free lactic acid which can react with the alcohol present. The reaction time is reduced from 10 hours to 1 hour. However, yield remains about 70% conversion overall to the ester. The Walkup process is preferably operated at 160–180° C. reaction temperature, with a 10:1 to 1:1 alcohol:acid ratio, and with a pressure of carbon dioxide of from 1 to 200 times atmospheric pressure.

Sterzel et al (U.S. Pat. No. 5,453,365, Sept. 26, 1995) describe a multi-step process for conversion of salts of organic acids to esters. The first step involves addition of calcium bicarbonate or similar species to a lactic acid producing fermentation to control the pH and form a crude aqueous solution of calcium salt of the lactic acid. In the second step, ammonia and carbon dioxide are added to the broth to reach a pH of 7 to 13 and to precipitate calcium carbonate. This calcium salt is removed by filtration or centrifugation for reuse in the fermentation. The crude ammonium lactate solution is then directly esterified with an alcohol. However this process gave significant levels of unwanted yield-reducing products such as lactamide. Therefore, an additional step was added to the process. This additional step involved displacing the ammonia with a trialkyl-amine. The trialkyl-amine does not react with the lactic acid to form amides. The ammonia is removed and then the solution containing the low molecular weight trialkyl-amine and the lactic acid is reacted with alcohol to produce ester.

The Sterzel patent indicates that the yield-reducing side reactions encountered by Filachione, Schulz, Walkup and Sterzel can be avoided by converting the ammonium lactate to the trialkyl-amine—lactate prior to esterification and also prior to the acid-base separation step. Sterzel et al then remove the base from the lactate by thermal decomposition wherein the low molecular weight trialkyl-amine is boiled overhead during the esterification. The esterification overhead contains four components—the ester, excess alcohol, water, and the trialkyl-amine.

Datta et al (U.S. Pat. No. 5,723,639, Mar. 3, 1998) describe use of pervaporation membranes for esterification to remove water. They also mention direct esterification of ammonium lactate with ethanol. However, the rates of pervaporation are relatively low, the cost of membranes is high, and the temperature required for ammonium lactate decomposition is greater than that for which membranes are currently available.

Two questions that are not addressed effectively in the above patents are (1) how to drive the removal of ammonia and (2) how to drive the esterification reaction to high levels of conversion, while in both cases minimizing the formation of unwanted side reaction products, and how to achieve this at high rates for either or both processes with relatively simple equipment. There is a long standing need for improved processes for producing and recovering organic acids and esters thereof.

SUMMARY OF THE INVENTION

One aspect of the present invention is a process for removing ammonia to produce a free organic acid, which may optionally be coupled with simultaneously producing an ester of the organic acid. The process comprises at least three steps:

(a) An aqueous diluent, an ammonium salt of an organic acid, and an alcohol are combined, thereby forming a liquid feed mixture. Preferably the liquid feed mixture is homogenous at the feed temperature.

(b) The feed mixture is rapidly heated (preferably at a rate of at least 10° C./minute) and optionally held at a pressure sufficient to suppress vaporization of at least a portion of is the alcohol, and preferably sufficient to suppress any substantial vaporization of the alcohol more than 5% w/w, wherein the mixture temperature and time sequence is sufficient to decompose the ammonium salt of the organic acid into ammonia and free organic acid while simultaneously removing the released ammonia. "Temperature and time sequence" in this context means that the temperature to which the feed mixture is heated, and the time for which it is maintained at that temperature, are sufficient to cause the desired decomposition of the ammonium salt. It is of course possible to have the temperature vary over the relevant time period, and such a non-constant temperature profile is included by the term "temperature and time sequence"in this patent. Optionally the temperature and time can also be sufficient to cause reaction of some of the free organic acid with the alcohol to form an ester of the organic acid. The result is production of (i) a vapor product stream that comprises ammonia, water, and alcohol, and (ii) a liquid product stream that comprises free organic acid, alcohol, and optionally ester, where of the total quantity of alcohol in the vapor product stream and the liquid product stream, at least about 10% by weight is present in the liquid product stream.

(c) The free organic acid and the ester (if ester is present) are recovered from the liquid product stream.

The liquid feed mixture can comprise a crude or partially purified broth produced by a fermentation process, or alternatively it can contain an ammonium salt of an organic acid from some other source.

The heating in step (b) can be performed by contacting the liquid feed mixture with an elevated temperature gas stream, which can comprise inert gas, alcohol vapor, carbon dioxide, or a mixture of any two or more thereof. Preferably the mass ratio of the elevated temperature gas stream to the feed mixture is no greater than about 0.4:1. It is especially preferred that the elevated temperature gas stream and the feed mixture flow countercurrent to each other in a reaction vessel.

The liquid product stream preferably comprises at least about 1.2 moles of alcohol (e.g., ethanol) per mole of lactic acid, and no more than about 20% water by weight.

One of the advantages of this process is its ability to recover free ammonia. Preferably the quantity of ammonia in the vapor product stream is equal to at least about 80 mole % of the quantity of ammonium ion in the feed. The ammonia recovered from the vapor product stream can optionally be recycled for use in forming the ammonium salt of the organic acid, for example in a fermentation process.

The quantity of the ester of the organic acid in the liquid product stream preferably is equal to at least about 10 mole % of the quantity of organic acid in the feed. The molar ratio of ammonium salt of organic acid to alcohol in the feed mixture preferably is between about 1:1 and about 1:10.

In one embodiment of the present invention, the organic acid is selected from the group consisting of mono-, di-, and tricarboxylic acids having 3–8 carbon atoms. In another embodiment, the organic acid is selected from the group consisting of acetic acid, succinic acid, citric acid, malic acid, lactic acid, hydroxyacetic acid, pyruvic acid, itaconic acid, formic acid, oxalic acid, propionic acid, beta-hydroxybutyric acid, and mixtures thereof.

The alcohol used in this embodiment of the present invention preferably is an aliphatic alcohol having from 1–20 carbon atoms, more preferably having from 1–12 carbon atoms. Examples of presently preferred alcohols are methanol, ethanol, n-propanol, i-propanol, n-butanol, t-butanol, i-butanol, pentanol, hexanol, octanol, dodecanol, and mixtures thereof. The alcohol acts to alter ammonia solubility and reduce the extent of side reactions.

In one particular preferred embodiment of the present invention, the alcohol is ethyl alcohol (ethanol), which can be naturally produced, and is readily available, and can produce an ester that is amendable to purification by distillation at moderate temperatures without use of high vacuum.

In one embodiment of the present invention, an inert gas can be used to help carry the ammonia out of the reaction vessel. In this embodiment, the gas may either be saturated with the alcohol being used in the system, or it may have a humidity of the alcohol solvent less than the dew point at the system temperature and pressure. In this latter case, the carrier gas can act to remove alcohol from the decomposed mixture and help in producing an organic acid product that has reduced levels of alcohol or ester. One example of this is the use of nitrogen to remove ethanol from the organic acid, allowing conversion of any esters of the organic acid into free acid and removal of the resultant alcohol. In this embodiment, the bottoms are produced that are largely free of the ester of the organic acid, even when the alcohol is used as the solvent.

In another embodiment of the present invention, a flow of alcohol vapor can be used instead of an inert gas to help carry the ammonia out of the reaction sphere. In this embodiment, the alcohol may be most conveniently introduced at the bottom of the reactor column system as a vapor stream that is either superheated or saturated condition.

In one embodiment of the process, the feed mixture is heated in step (b) to a temperature greater than about 100° C., more preferably to a temperature between about 150–280° C., most preferably to a temperature between about 155–220° C. It is also preferred that step (b) take place in a reaction vessel and the pressure in the vessel be greater than about 100 psig, and less than about 1,800 psig. More preferably the pressure in the vessel is between about 200–600 psig. Examples of suitable reaction vessels include distillation columns and falling film evaporators. Trayed distillation columns with heated pump-around loops on one or more of the tubes are one preferred type of equipment. Preferably the average residence time of the feed mixture in the reaction vessel is between about 0.5–30 minutes. Preferably the liquid feed is not preheated prior to entering the reaction vessel, but is then rapidly heated in that vessel. Preferably the rate of heating in the reaction vessel is at least about 10 ° C./minute.

It is possible to use a plurality of reactors in series. Thus, in one embodiment, the liquid product stream is incorporated into a second feed mixture that is heated as in step (b), thereby producing a second vapor product stream that comprises ammonia, water, and alcohol, and a second liquid product stream that comprises free organic acid, ester, and alcohol. The second liquid product stream optionally can be incorporated into a third feed mixture that is heated as in step (b), thereby producing a third vapor product stream that comprises ammonia, water, and alcohol, and a third liquid product stream that comprises free organic acid, ester, and alcohol. Further stages can be added as needed.

One notable feature of the present invention is its ability to recover acid while minimizing degradation of the acid's optical purity. In one embodiment, the optical purity of the products (organic acid product and the ester of the organic acid in the liquid product stream) are no more than 0.5% greater than the optical purity of the feed (ammonium salt of the organic acid in the feed).

In one particular embodiment of the invention, the liquid product stream is fed to a plug flow reactor vessel in which at least some unreacted organic acid reacts with at least some unreacted alcohol to form additional ester of the organic acid, whereby an equilibrium reaction mixture is produced. Optionally a vapor stream can be removed from the equilibrium mixture, the vapor stream comprising ester of the organic acid, unreacted alcohol, and water, and the unreacted organic acid recovered and recycled to the plug flow reactor.

In another particular embodiment, the liquid product stream further comprises an amide of the organic acid, and at least some of the amide is converted to an ester of the organic acid by addition of a mineral acid such as sulfuric acid.

In one embodiment, the mode of heat transfer to the reactants can be analogous to what occurs in a stripping distillation column (e.g., a packed column). In another embodiment, the mode of heat transfer can be analogous to what occurs in an evaporator (e.g., hollow tubes, no packing). In yet another embodiment, the heat transfer can occur through heated tubes and be facilitated by packing within the tubes. In another, the heating can be on external heat exchangers that are fed from and to trayed stages in a distillation column. This is called a pump-around.

In any of these equipment embodiments, pressure and temperature may be controlled to prevent substantial vaporization of alcohol and the carrier gas used to sweep the ammonia away from the reaction region. However, it is also possible in any of these embodiments to control the pressure and temperature at levels such that a significant amount of vaporization of alcohol occurs, and the vaporized alcohol flow is used to help sweep the ammonia away from the reaction region.

A presently preferred specific embodiment of the invention is a process for producing lactic acid and an ester thereof, comprising the steps of:

(a) combining (i) an aqueous fermentation broth comprising ammonium lactate, and (ii) an aliphatic alcohol having from 1–12 carbon atoms, thereby forming a liquid feed mixture;

(b) contacting in countercurrent flow the liquid feed mixture in a reaction vessel with an elevated temperature gas stream that comprises inert gas, alcohol vapor, carbon dioxide, or a mixture of any two or more thereof;

(c) heating the feed mixture in the reaction vessel to about 150–280° C. at a pressure of about 200–600 psig, where the average residence time of the feed mixture in the reaction vessel is from about 0.5–30 minutes, thereby producing (i) a vapor product stream that comprises ammonia, water, and alcohol, and (ii) a liquid product stream that comprises free lactic acid and lactate ester; and (d) recovering the free lactic acid and the lactate ester from the liquid product stream.

In this process, the heating of step (c) can be accomplished solely by heat transfer from the elevated temperature gas stream to the liquid feed mixture, or it can be accomplished at least in part by passing the liquid feed mixture through a heat exchanger that is external to the reaction vessel.

The present invention can achieve high yields of free organic acid and optionally esters of the organic acid, with minimal production of unwanted side reaction products, such as amides. The process also achieves high rates and extents of release of free ammonia, which can be recycled for use in neutralization during fermentation.

In the present invention, reaction (3) described above is minimized. Further, rather than reaction (2), the present invention achieves to a significant extent reaction (7), in which the alcohol is not consumed in the reaction.

ammonium salt of organic acid+alcohol→free acid+ammonia+ alcohol                      Reaction (7)

In practice, to some extent all four reactions (1), (2), (3), and (7) occur, but in such yields and rates as to be very attractive economically.

The present invention involves the thermal decomposition of the ammonium salts of organic acids, combined with esterification to form esters of the organic acid. The use of a short contact time and a temperature high enough to obtain rapid and substantially complete decomposition of the ammonium salt into ammonia and free acid are important features of an embodiment of the process.

The method described herein can apply to any organic acid that may be present as an ammonium salt. Relatively highly volatile organic acids, such as acetic acid, which also have volatile esters such as ethyl acetate, can be produced in the present invention by controlling the temperature and pressure of the system to ensure sufficient decomposition and also to suppress excessive vaporization.

The present invention can significantly lower the cost of production of lactic acid and other organic acids compared to previous state-of-the-art methods for producing free acid.

DESCRIPTION OF SPECIFIC EMBODIMENTS

The following definitions are used in this patent. "Lactic acid" refers to the monomeric free lactic acid as is commonly found is dilute aqueous solutions. "88% lactic acid" and "lactic acid of commerce" refer to a typical commercially available lactic acid, which is actually a mixture of monomeric lactic acid, linear dimer lactic acid or lactoyl lactic acid, short chain lactic acid oligomers, water, and also a small quantity of cyclic dimer lactic acid or lactide. When this lactic acid is diluted in a large excess water, it will slowly hydrolyze or convert to all monomeric form lactic acid.

Production of an organic acid such as lactic acid by fermentation is well known. A person skilled in the art will be familiar with reactants, equipment, and process conditions suitable for such fermentation. The result of the fermentation will be an aqueous broth that comprises the acid, typically in the form of a salt, in addition to inorganic salts, protein fragments, sugar residues, other organic acids and alcohols, ketones, and metal ions. The broth can be purified, for example by filtration, to remove some of the impurities, and can also be concentrated.

The present invention provides means for recovering the organic acid and/or an ester thereof from the purified broth. However, it should be understood that the present invention is not limited to use in conjunction with fermentation, nor is it limited to use with broth that has been purified and/or concentrated.

Figure 1:
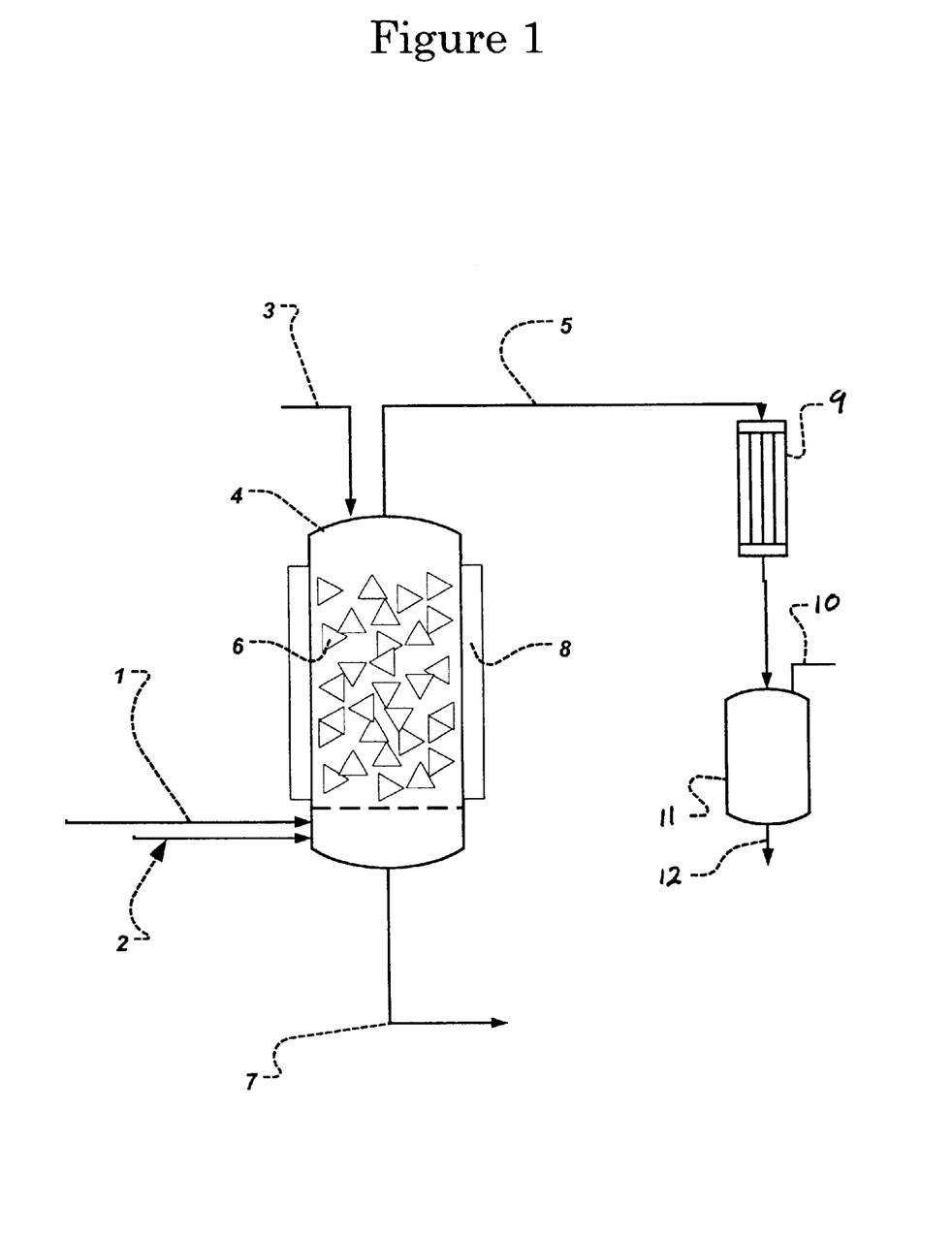
FIG. 1 is a process flow diagram for an organic acid process in accordance with the present invention.

One embodiment of a process of the present invention is shown schematically in FIG. 1.

Concentrated crude ammonium salt of the organic acid and alcohol are mixed and optionally heated to the bubble point and fed as stream 3 to stripper-reactor vessel 4. Optionally a miscible non-alcohol diluent or solvent that is non reactive may also be used, such as chloroform or methyl-isobutylketone. The vessel 4 may be, for example, an evaporator with countercurrent or co-current strip gas flow or a distillation column with inter-stage heating. Mass transfer must be sufficiently rapid such that the ammonia is transferred to the vapor phase. Temperatures must be sufficient for rapid decomposition of the ammonium salt.

Stripper-reactor vessel 4 may optionally include packing 6 and jacketed heating 8. The heating jacket 8 may be replaced by pump-arounds with heating. The packing 6 may be replaced with trays or there may be no packing at all. In the case of no packing, suitable mass transfer occurs due to operation in an evaporation mode wherein the liquid runs down the walls of tubes in vessel 4 and the vapor and gases travel in the central region of the tubes.

In one particular embodiment, the vessel 4 is a modified falling film evaporator wherein the evaporation tubes are packed with mass transfer enhancing packing. The tube diameter preferably is from about 0.5 to 3 inch, the tubes are heated with steam or other heat transfer fluid on the outer side, and they are packed with a suitable distillation packing on the inside. Examples of suitable packing include saddles, rings, other random packing from 0.05 to 0.5 inch nominal dimension, structured sheet packing (e.g. Koch Flexipac™), and coiled wire packing (e.g. Goodloe™ packing).

To the bottom of the vessel 4 is optionally fed hot dry inert gas stream 1, or hot saturated or superheated dry alcohol vapor stream 2, or a combination of both. The rate and extent of these feeds depends on the exact design of vessel 4. If there is less heating in vessel 4, then additional heat can be supplied by these streams.

Optionally a basic catalyst can be added to increase the rate of esterification.

From the bottom of vessel 4 a liquid product stream 7 is removed which contains alcohol, free organic acid, optionally some ester other non-volatile components present in the feed solution, and some of the optional inert gas that may be dissolved in stream 7. Some amount of ester will usually be produced, but if it is desired to have substantial ester production, the process conditions will need to be adjusted (e.g., increase in residence time and/or temperature).

From the top of vessel 4 is withdrawn a vapor stream 5 that contains alcohol, water, ammonia, volatile impurities present in the feed, and optionally inert gas. This stream 5 is then treated in any of a variety of ways apparent to one skilled in the art to recover ammonia from the other components present. By way of example, the alcohol might be condensed in condenser 9 and the ammonia removed as the vapor overhead 10 from alcohol receiver 11, while the condensed alcohol 12 is further treated to strip the residual ammonia dissolved therein.

Optionally there may be more than one such reactor 4 operated in series, wherein the bottoms product stream 7 from the first reactor becomes the feed stream 3 to a second reactor similar to the first.

In one specific embodiment of the invention, ethanol (dry or 94% w/w) and concentrated ammonium lactate (70–95% w/w in water) are blended carefully to give a feed mixture 3 that contains from 10 to 25% ammonium lactate in ethanol with relatively low levels of water, optionally preheated, and fed to the top of a packed stripping column 4 operating at 155–220° C. Temperatures must be hot enough to obtain ammonia release, but low enough to avoid lactic acid decomposition.

Hot nitrogen gas 1 is fed to the bottom of the stripping reactor 4 at a mass ratio of 0.0 to about 0.4 to the feed stream 3. The column 4 preferably is operated at a pressure that suppresses substantial vaporization of alcohol. This is very important as the alcohol (e.g., ethanol) aids the decomposition, it seems, by preventing formation of oligomers and viscous and acidic materials, and also it affects the solubilities. An example of a suitable range of pressure is between about 200 and about 600 psig.

The hot nitrogen gas flows up the column and travels to the overhead condenser 9. This overhead stream contains ammonia, ethanol, water, and nitrogen. The components are separated by techniques well known in the art, either at elevated pressure or at lower pressures.

The liquid travels down the column. The bottoms product 7 is a mixture of ethanol, water, lactic acid, ethyl lactate, and some ammonia. Low levels of lactamide may or may not also be present.

The heat input and the pressure in the column 4 are controlled so that the amount of ethanol in the overhead condensate can be varied. The high temperature gives rapid ammonia release. The ethanol serves to react with the lactic acid and also to decrease the solubility of nitrogen and of ammonia in the liquid stream.

Note that any alcohol can be used in this reactor. For higher molecular weight, less volatile alcohols (for example molecular weight above about 100 gram/mol), the inert strip gas flowrate must be increased to carry the ammonia out. For lower molecular weight alcohols (e.g., molecular weight below about 100 gram/mol), either the alcohol or the inert gas can act to carry the ammonia out of the system. This choice depends in part on the choice of system temperature and pressure. A suitable operating temperature is chosen for the particular organic acid and then the pressure and strip gas choice must be adjusted to achieve the desired performance.

The invention can be further understood from the following examples.

EXAMPLE 1

A vertical stripper-contactor reactor was constructed. It was 3/8 inch OD stainless steel, and packed with 12 inches depth of ProPak 316 stainless steel gauze mass transfer packing. A continuous liquid feed was introduced to the top of the column at 1.0 ml/minute using a high pressure metering pump. Reactor residence time for the liquid in the packing was estimated to be on the order of 25 to 50 seconds, depending on the liquid and vapor flowrates, which depend on the feed rates, rate of inert gas, system temperature, and system pressure.

The liquid feed to the top of the column contained the following components: 48 gram of 80% ammonium lactate obtained from Pflautz and Bauer and 356 gram of anhydrous ethanol. To the lower section of the stripping column a hot nitrogen gas was introduced at 150° C. and a flowrate of 0.16 gram/minute. The column walls were heated in two sections, each controlled using a thermocouple probe attached to the outer surface of the column. The column was insulated with 2 inches of glass fiber insulation. The upper and lower sections were heated with a constant current, constant voltage source to give a constant heat input load. The consequent temperature was observed. The overhead vapor was withdrawn and condensed in a water cooled condenser operating at 16° C. The uncondensed gases were then passed into an overhead vapor line past a pressure gauge and pressure relief valve to an acid trap. The acid trap contained 0.5 M sulfuric acid in water that was used to capture any ammonia that did not dissolve in the condensed ethanol. The gases exiting from the acid trap then passed to a pressure letdown valve and to a gas flowmeter. The system pressure was regulated at 150 psig. The hot nitrogen inlet gas temperature was controlled at 152° C.

The overhead condensate, liquid bottoms, feed, and trap liquor were all analyzed for ammonia level. It was found that the extent of decomposition conversion of the ammonium lactate in the feed into free ammonia from three runs was less than 10% on average.

This shows that if the temperature is too low, then decomposition does not proceed readily in this stripper reactor equipment.

EXAMPLE 2

The stripper reactor test of Example 1 was repeated with a higher system pressure of 162 psig. The overhead vapor temperature was observed to be 152–155° C. The same feed composition, feed rate, and nitrogen rate was used. Approximately 67% of the total mass present in the feed stream ended up in the condensate. A total of 43.7% of the ammonia present in the feed was collected in the trap and the condensate. The nitrogen inlet temperature was controlled at 151° C.

EXAMPLE 3

The stripper reactor test of Example 2 was repeated with a system pressure of 162 psig. The heat load to the reactor walls was reduced. The overhead vapor temperature was 101° C. and the fraction of the feed mass ending up as condensate was on average 23% of the total feed mass. A total of 20.9% of the ammonia present in the feed was collected in the trap and the condensate. This indicates that with the stripper-reactor used, the vapor temperature is important to determine the extent of conversion. The nitrogen inlet temperature was controlled at 142° C. Supplying sufficient heat to the jacket of the decomposer-reactor is necessary to obtain good decomposition as was obtained in Example 2.

EXAMPLE 4

A fresh feed was prepared by reacting 88% lactic acid with equimolar 28% aqueous ammonia. The heat of reaction raised the temperature above room temperature. The mixture was then gently refluxed to ensure that all dimer and oligomer lactic acid was converted into monomeric ammonium lactate. The resultant ammonium lactate contained significant levels of lactamide. Of the total nitrogen present in the feed, 10.4% was present as lactamide. The mixture was concentrated and adjusted to give 84% W/W ammonium lactate solution in water This feed was mixed with 90% ethanol, 5% methanol, and 5% iso-propanol to produce a solution that was 1.2 mole/liter concentration in ammonium lactate. A total of 182.6 grams of this feed was fed continuously over a period of 3.5 hours to the stripper reactor. A total of 62.4 grams of condensate were collected and 120.2 grams of liquid exiting the bottom of the reactor. The system pressure was 220 psig and the overhead vapor temperature was 154° C. The nitrogen feed temperature was set at 169° C.

A total of 56.8% of the ammonia present in the feed was removed into the overhead condensate and trap streams. There was little or no increase in the total mass of lactamide present in bottoms as compared to that present in the feed. The bottoms contained 0.94% w/w free ammonia. The feed contained 1.83% w/w free ammonia.

EXAMPLE 5

Example 4 was repeated with pure ethanol instead of 90% ethanol, 5% methanol, and 5% iso-propanol. Results similar to those of Example 4 were obtained.

EXAMPLE 6

Example 4 was repeated with a feed mixture that was 0.8 mole/liter ammonium lactate and 0.4 mole/liter free lactic acid. This was to determine if the presence of free lactic acid tended to reduce the rate of ammonia removal or decomposition as compared to Example 4. Temperatures and flowrates were similar except that the vapor temperature now averaged 158° C. rather than 154° C. A total of 190.4 grams of feed were fed, and 59.0 grams of overhead condensate and 131.4 grams of bottoms were collected. Of the total nitrogen in the feed, only 30.7% was removed in this decomposition run.

EXAMPLE 7

Example 6 was repeated with a feed mixture that was 0.4 mole/liter ammonium lactate and 0.8 mole/liter free lactic acid. This was to determine if the presence of free lactic acid tended to reduce the rate of ammonia removal or decomposition as compared to Examples 4 and 6. Temperatures and flowrates were similar except that the vapor temperature now averaged 163° C. rather than 154° C. and 158° C. as in the two comparison examples. A total of 189.5 grams of feed were fed, and 58.7 grams of overhead condensate and 130.8 grams of bottoms were collected. Of the total nitrogen in the feed, only 20.4% was removed in this decomposition run.

This example shows that the presence of lactic acid tends to make the removal of free ammonia more difficult as compared to the presence of ammonium lactate. Therefore, a process that can convert the free lactic acid to ethyl lactate or other species will tend to enhance the removal of ammonia from the system.

EXAMPLE 8

This example involved a sequence showing the effect of repeated reaction-stripping. The system pressure in the reactor-stripper was raised from 1.65 MPaa (220 psig) to 2.44 MPaa (340 psig) to reach a temperature of 180 to 185° C. in the reactor zone. Feed was 1.2 M ammonium lactate to the first experiment (example 8a). The bottoms from example 8a, 37.0 grams, were used as feed to example 8b, with 31.8 gram of ethanol added, to make a total feed for example 8b of 68.8 grams. The bottoms from example 8b, 47.8 grams, were used as feed to example 8c, with 18.1 grams of added ethanol. The nitrogen gas temperature in each case was controlled at 180° C. The overhead vapor temperature in each case was from 171 to 173° C.

In the table below, "FD" refers to feed, "BT" refers to bottoms, "OV" refers to overhead, and "TR" refers to trap. The number appearing after these abbreviations refers to the example.

| Stream | FD8a | BT8a | OV8a | TR8a |
| --- | --- | --- | --- | --- |
| Mass, gram | 73.0 | 37.0 | 36.1 | 13.7 |
| free NH3, mmol | 75.11 | 14.0 | 77.6 | 6.43 |
| Lactamide, mmol | 12.6 | 21.0 | 0.0 | 0.0 |
| Stream | FD8b | BT8b | OV8b | TR8b |
| Mass, gram | 68.8 | 47.8 | 20.0 | 18.1 |
| free NH3, mmol | 13.07 | 3.39 | 4.51 | 1.90 |
| Lactamide mmol | 17.5 | 14.0 | 0.0 | 0.0 |
| Stream | FD8c | BT8c | OV8c | TR8c |
| Mass, gram | 65.9 | 31.4 | 34.5 | 33.0 |
| free NH3, mmol | 3.18 | 1.01 | 1.48 | 0.46 |
| Lactamide, mmol | 17.4 | 16.7 | 0.7 | 0.0 |

Note that FD8a contained 75.11 mmol of $NH_3$, while stream BT8c had 1.01 mmol of $NH_3$. This shows that 98.6% of the free ammonia was removed in this three stage process. Note that the level of lactamide may have increased somewhat, however there was considerable scatter in the analytical method for lactamide. In fact, the total quantity of lactamide appeared to decrease in each of examples 8b and 8c If it increased, it was only by a relatively small amount. This reflects one of the advantages of this invention, that low levels of unwanted by-products are formed. This occurs by use of carefully designed mass transfer equipment.

The feed stream to Example 8a and the bottoms stream were assayed for the fraction of D-lactic to total lactic acid by an enzymatic assay. The result showed that the extent of racemization increased by 0.31% for the three passes of the reactor-decomposer. Chromatographic analysis of the products from the three successive passes showed that in each pass about 5% of the total moles of lactic acid was converted to ethyl lactate.

| Stream | Ratio of moles ethyl lactate to total moles of ethyl lactate and lactic acid |
| --- | --- |
| Feed Solution to Example 8a | 0.0% |
| Average analysis after Example 8a | 5.4% |
| Average analysis after Example 8b | 9.8% |
| Average analysis after Example 8c | 14.6% |

EXAMPLE 9

This example differed from example 8a in that a newly prepared ammonium lactate was used. In both cases the ammonium lactate was prepared by mixing ammonium hydroxide 30% with lactic acid, 50% or 88%. The mixture was then heated gently to allow conversion of the dimer lactic acid and dimer ammonium lactate to monomer ammonium lactate. If this heating is done too quickly, some ammonia may be driven off before dimer is converted. The ammonium lactate broth was then concentrated. The final concentration for this example was somewhat higher than the example 8a case. Operation was at 220 psig as in example 8a.

The ammonium lactate broth for this example was analyzed to contain 15.5% ammonia, (which would be equimolar with 81–82% lactic acid), and 2.2% lactamide. This feed most likely contained ammonium lactoyl-lactate as well as ammonium lactate.

The lactamide level in this mixture was similar to that of less concentrated mixtures. This suggests that the lactamide formation occurs when the 30% ammonium hydroxide is blended into the 50% or 88% lactic acid.

The concentrated ammonium lactate broth was mixed with ethanol as usual to form a mixture that was near to 10% w/w ammonium lactate in ethanol, and fed to the stripper reactor.

This example was operated at nearly identical heater settings to examples 8a, 8b, and 8c. However, for this example, there was a substantially higher level of overhead and less bottoms (56 gram of bottoms and 153 gram of overhead). This may have been due to a low water content in the feed. Less latent heat is required for evaporation of ethanol than for water, and thus a given heat input will evaporate more ethanol than water.

Despite these differences, 91% of the free ammonia mass was removed in the overhead. The total mass of lactamide was essentially unchanged during the decomposition (4.85 gram in and 4.90 gram out). The trap contained 3% of the total ammonia present in the feed.

EXAMPLE 10

This example used some extra feed that had been prepared for example 8a. The feeds to examples 8a and 10 were thus identical. In this example 10, no lactamide formation was observed. This example was operated at 340 psi and 179–182° C. The heat settings were lowered very slightly from earlier runs. There was in this run only a small amount of overhead condensate, 11.6 grams, compared to 111.3 grams of bottoms residue. The bottoms contained 10% of the total ammonia fed to the system, thus 90% was removed in the overhead. For this example, however, the small volume of condensate led to additional ammonia load on the trap. It appears that the trap became saturated with ammonia and then the majority of the ammonia was lost in the vent line. In total, 23% of the ammonia was collected in the trap, and apparently 58% of the ammonia was lost in the system vent.

Example 9 and this example confirm the results seen for Example 8a, that 90% ammonia removal can be achieved from the reaction feed in a single pass of a short time stripper reactor. They also show that there is no appreciable increase in lactamide levels during this reaction time. This example shows that the system can be operated at low ethanol overhead rates.

EXAMPLE 11

In this example, conditions were similar to those of Example 2, except that there was a temperature perturbation in the equipment. Temperatures reached as much as 240° C. High levels of ethyl lactate were produced. The bottoms from this example contained: free lactic acid 540 gram/liter, ethyl lactate 270 gram/liter, and lactamide 70gram/liter. This shows that even with a residence time in the reactor of less than 50 seconds, ethyl lactate can be produced readily.

EXAMPLE 12

Conversion of lactic acid and ethanol from decomposer

Typically in the above experiments we see anywhere from $\frac{1}{20}$ to $\frac{1}{4}$ of the lactic acid converted to ethyl lactate. Kinetic data from for the conversion of 85% lactic acid and ethanol into ethyl lactate is presented by Troupe and DiMilla, (1957, Industrial and Engineering Chemistry, Volume 49, No. 5, page 847). This data can be fitted to an appropriate kinetic model and then used to predict esterification rates at different temperatures and catalyst levels. Extrapolation of this data, developed for strong acid catalysed conversion at 20 to 100° C., to the situation of weak lactic acid as a catalyst with ethanol at 180° C., indicate that 3.5 minutes are required to reach a 90% approach to reaction equilibrium from specified initial conditions. Note that this reaction is catalysed by free lactic acid. As the lactic acid concentration decreases due to formation of ethyl lactate, the rate of esterification will decrease as there will be less catalyst. This prediction is in reasonable agreement with our measured conversion of 5% of the lactic acid in the 20–40 seconds residence time in our reactor-stripper unit.

EXAMPLE 13

This example shows that we can also bias this reaction in the other direction, and while some ethyl-lactate is produced in the top section of the reactor, in the lower section during this run we found that the hot dry nitrogen gas admitted at the bottom of the column was acting to strip away any ethanol present. This drives the reverse reaction, namely the hydrolysis of any ethyl-lactate present to free lactic acid.

The feed to this run contained 23% w/w ammonium lactate, provided as a 90% w/w aqueous solution and then dissolved in ethanol to form a homogeneous mixture. In this run over 93% removal of ammonia was achieved and the bottoms contained the following:

Lactic acid 55.8% w/w
Ethyllactate 2.35% w/w

Lactic dimer, residual ethanol, water, lactamide, and ammonia—balance

We thus see that compared to some of our other runs, the formation of ethyl-lactate has been reduced dramatically, while at the same time a more concentrated product is produced.

EXAMPLE 14

The product from the reactor-decomposer can be held in a plug flow reactor for conversion of the unreacted lactic acid to form an equilibrium mixture. This mixture can be then flashed in a flash drum and the ethyl lactate, ethanol, and water taken overhead. Unreacted lactic acid can be recycled to the plug flow reactor together with freshly decomposed ammonium lactate-ethanol-ethyl lactate mixture. The system does not need added catalyst as the free lactic acid acts as a catalyst. This has the advantage that the rapid cooling in the flash unit will drop the temperature to 120° C. or less, essentially stopping any reaction.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A process for producing an organic acid, comprising the steps of:
    (a) combining an aqueous diluent, an ammonium salt of an organic acid, and an alcohol, thereby forming a liquid feed mixture;
    (b) heating the feed mixture at a pressure sufficient to suppress vaporization of at least a portion of the alcohol with a temperature and time sequence sufficient to decompose the ammonium salt of the organic acid into ammonia and free organic acid, while simultaneously contacting the liquid feed mixture with a flowing gas stream and removing the ammonia, thereby producing (i) a vapor product stream that comprises ammonia, water, and alcohol, and (ii) a liquid product stream that comprises free organic acid and alcohol, where of the total quantity of alcohol in the vapor product stream and the liquid product stream, at least about 10% by weight is present in the liquid product stream; and
    (c) recovering the free organic acid from the liquid product stream.

2. The process of claim 1, where the mixture is held in step (b) at a temperature and for a time sufficient to react at least some of the free organic acid with the alcohol to form an ester of the organic acid, the ester being present in the liquid product stream.

3. The process of claim 2, where ester is recovered from the liquid product stream in step (c).

4. The process of claim 1, where the pressure in step (b) is sufficient to suppress any vaporization of the alcohol more than 5% by weight.

5. The process of claim 1, where the pressure in step (b) is greater than 100 psig.

6. The process of claim 1, where the heating in step (b) is performed by contacting the liquid feed mixture with an elevated temperature gas stream.

7. The process of claim 6, where the elevated temperature gas stream comprises inert gas, alcohol vapor, carbon dioxide, or a mixture of any two or more thereof.

8. The process of claim 6, where the mass ratio of the elevated temperature gas stream to the feed mixture is no greater than about 0.4:1.

9. The process of claim 6, where the elevated temperature gas stream and the feed mixture flow countercurrent to each other in a reaction vessel.

10. The process of claim 1, where the quantity of ammonia in the vapor product stream is equal to at least about 80 mole % of the quantity of ammonium in the feed.

11. The process of claim 1, where ammonia is recovered from the vapor product stream and is recycled for use in forming the ammonium salt of the organic acid.

12. The process of claim 1, where the quantity of the ester of the organic acid in the liquid product stream is equal to at least about 10 mole % of the quantity of the organic acid in the feed.

13. The process of claim 1, where the molar ratio of ammonium salt of organic acid to alcohol in the feed mixture is between about 1:1 and about 1:10.

14. The process of claim 1, where the liquid feed mixture comprises a crude or partially purified broth produced by a fermentation process.

15. The process of claim 1, where the organic acid is selected from the group consisting of mono-, di-, and tricarboxylic acids having 3–8 carbon atoms.

16. The process of claim 1, where the organic acid is selected from the group sting of:
    acetic acid, succinic acid, citric acid, malic acid, lactic acid, hydroxyacetic acid, pyruvic acid, itaconic acid, formic acid, oxalic acid, propionic acid, beta-hydroxybutyric acid, and mixtures thereof.

17. The process of claim 1, where the alcohol is an aliphatic alcohol having from 1–20 carbon atoms.

18. The process of claim 17, where the aliphatic alcohol has from 1–12 carbon atoms.

19. The process of claim 1, where the alcohol is selected from the group consisting of:
    methanol, ethanol, n-propanol, i-propanol, n-butanol, t-butanol, i-butanol, pentanol, hexanol, octanol, dodecanol, and mixtures thereof.

20. The process of claim 1, where the feed mixture is heated in step (b) to a temperature greater than about 100° C.

21. The process of claim 20, where the feed mixture is heated in step (b) to a temperature between about 150–280° C.

22. The process of claim 21, where the feed mixture is heated in step (b) to a temperature between about 155–220° C.

23. The process of claim 1, where step (b) takes place in a reaction vessel and the pressure in the vessel is between about 100–1,800 psig.

24. The process of claim 23, where the pressure in the vessel is between about 200–600 psig.

25. The process of claim 23, where the reaction vessel is selected from the group consisting of a distillation column and a falling film evaporator.

26. The process of claim 23, where the reaction vessel is a trayed distillation column with heated pump-around loops on one or more of the trays.

27. The process of claim 23, where the average residence time of the feed mixture in the reaction vessel is between about 0.5–30 minutes.

28. The process of claim 23, where the liquid feed is not preheated prior to entering the reaction vessel, but is then heated in that vessel at a rate of at least about 10° C./minute.

29. The process of claim 23, where at least some ester of the organic acid is removed from the reaction vessel in the vapor product stream.

30. The process of claim 1, where ammonia is also removed from the reaction vessel by extraction.

31. The process of claim 2, where ester is removed from the reaction vessel by extraction.

32. The process of claim 1, where the liquid product stream is incorporated into a second feed mixture that is heated as in step (b), thereby producing a second vapor product stream that comprises ammonia, water, and alcohol, and a second liquid product stream that comprises free organic acid, ester, and alcohol.

33. The process of claim 32, where the second liquid product stream is incorporated into a third feed mixture that is heated as in step (b), thereby producing a third vapor product stream that comprises ammonia, water, and alcohol, and a third liquid product stream that comprises free organic acid, ester, and alcohol.

34. The process of claim 1, where a basic catalyst is added to the feed mixture.

35. The process of claim 1, where the optical purity of the organic acid in the liquid product stream is no more than 0.5% greater than the optical purity of the ammonium salt of the organic acid in the feed.

36. The process of claim 2, where the liquid product stream is fed to a plug flow reactor vessel in which at least some unreacted organic acid reacts with at least some unreacted alcohol to form additional ester of the organic acid, whereby an equilibrium reaction mixture is produced.

37. The process of claim 36, where a vapor stream is removed from the equilibrium mixture, the vapor stream comprising ester of the organic acid, unreacted alcohol, and water, and where unreacted organic acid is recovered and recycled to the plug flow reactor.

38. The process of claim 1, where the liquid product stream further comprises an amide of the organic acid, and at least some of the amide is converted to an ester of the organic acid by addition of a mineral acid.

39. The process of claim 1, where the liquid feed mixture further comprises a non-alcohol solvent.

40. A process for producing lactic acid and an ester thereof, comprising the steps of:
 (a) combining (i) an aqueous fermentation broth comprising ammonium lactate and (ii) an aliphatic alcohol having from 1–12 carbon atoms, thereby forming a liquid feed mixture;
 (b) contacting in countercurrent flow the liquid feed mixture in a reaction vessel with an elevated temperature gas stream that comprises inert gas, alcohol vapor, carbon dioxide, or a mixture of any two or more thereof;
 (c) heating the feed mixture in the reaction vessel to about 150–280° C. at a pressure of about 200–600 psig, where the average residence time of the feed mixture in the reaction vessel is from about 0.5–30 minutes, thereby producing (i) a vapor product stream that comprises ammonia, water, and alcohol, and (ii) a liquid product stream that comprises free lactic acid and lactate ester; and
 (d) recovering the free lactic acid and the lactate ester from the liquid product stream.

41. The process of claim 40, where the heating of step (c) is accomplished solely by heat transfer from the elevated temperature gas stream to the liquid feed mixture.

42. The process of claim 40, where the heating of step (c) is accomplished at least in part by passing the liquid feed mixture through a heat exchanger that is external to the reaction vessel.

43. The process of claim 40, wherein the liquid feed is not preheated prior to entering the reaction vessel, but is then heated in that vessel at a rate of at least about 10° C./minute.

* * * * *

UNITED STATES PATENT AND TRADEMARK OFFICE
CERTIFICATE OF CORRECTION

PATENT NO. : 6,291,708 B1
DATED : September 18, 2001
INVENTOR(S) : Michael Charles Milner Cockrem It is certified that error appears in the above-identified patent and that said Letters Patent is hereby corrected as shown below:

Claim 16,
Line 2, delete "sting" and insert therefor -- consisting --.

Signed and Sealed this

Twelfth Day of March, 2002

Attest:

Attesting Officer

JAMES E. ROGAN
Director of the United States Patent and Trademark Office